United States Patent [19]
Lee et al.

[11] Patent Number: 5,226,899
[45] Date of Patent: Jul. 13, 1993

[54] CATHETER TUBING OF CONTROLLED IN VIVO SOFTENING

[75] Inventors: Min-Shiu Lee, Spring Valley; Mutlu Karakelle, Dayton; David E. Spielvogel, Springboro; Robert A. Taller, Centerville, all of Ohio

[73] Assignee: Becton, Dickinson and Company, Franklin Lakes, N.J.

[21] Appl. No.: 746,813

[22] Filed: Aug. 15, 1991

Related U.S. Application Data

[63] Continuation of Ser. No. 499,145, Mar. 26, 1990, abandoned.

[51] Int. Cl.$^5$ ............................................. A61M 25/00
[52] U.S. Cl. .................................... 604/282; 604/264; 604/280
[58] Field of Search ............... 604/264, 265, 280, 282; 138/123-126, 172, 174

[56] References Cited

U.S. PATENT DOCUMENTS

| | | | |
|---|---|---|---|
| 3,825,036 | 7/1974 | Stent | 138/174 |
| 4,211,741 | 7/1980 | Ostoich . | |
| 4,371,686 | 2/1983 | Yamamoto et al. | 528/76 |
| 4,424,305 | 1/1984 | Gould et al. | 525/127 |
| 4,454,309 | 6/1984 | Gould et al. . | |
| 4,657,024 | 4/1987 | Coneys . | |
| 4,668,221 | 5/1987 | Luther . | |
| 4,689,386 | 8/1987 | Chapman et al. | 528/71 |
| 4,728,322 | 3/1988 | Walker et al. . | |
| 4,780,512 | 10/1988 | Gould et al. | 525/454 |
| 4,781,703 | 11/1988 | Walker et al. . | |
| 4,789,720 | 12/1988 | Teffenhart | 528/76 |
| 4,790,817 | 12/1988 | Luther | 604/53 |
| 4,790,831 | 12/1988 | Skribiski | 604/282 |
| 4,798,597 | 1/1989 | Vaillancourt | 604/265 |
| 4,798,876 | 1/1989 | Gould et al. | 525/457 |
| 4,810,582 | 3/1989 | Gould et al. | 128/849 |
| 4,883,699 | 11/1989 | Aniuk et al. . | |
| 4,898,591 | 2/1990 | Jang et al. | 604/282 |
| 4,900,314 | 2/1990 | Quackenbush | 604/282 |
| 4,944,278 | 7/1990 | Woodard | 464/57 |
| 4,976,703 | 12/1990 | Franetzki et al. | 604/265 |
| 4,990,143 | 2/1991 | Sheridan | 604/282 |
| 4,994,047 | 2/1991 | Walker et al. | 604/264 |

OTHER PUBLICATIONS

Du Pont Engineering Polymers, Hytrel Polyester Elastomer, General Guide to Products & Properties, Sep. 1984.

Primary Examiner—C. Fred Rosenbaum
Assistant Examiner—Ronald Stright, Jr.
Attorney, Agent, or Firm—Richard E. Brown

[57] ABSTRACT

A catheter tubing has a layer of a hydrophobic stiffening polymer encapsulated by a layer of hydrophilic thermoplastic base polymer. Preferred stiffening polymers are polyesterpolyether block copolymers. Preferred base polymers are thermoplastic polyetherurethanes. The encapsulated layer may be a stripe or an annular layer having base polymer layers laminated on both surfaces thereof.

1 Claim, 2 Drawing Sheets

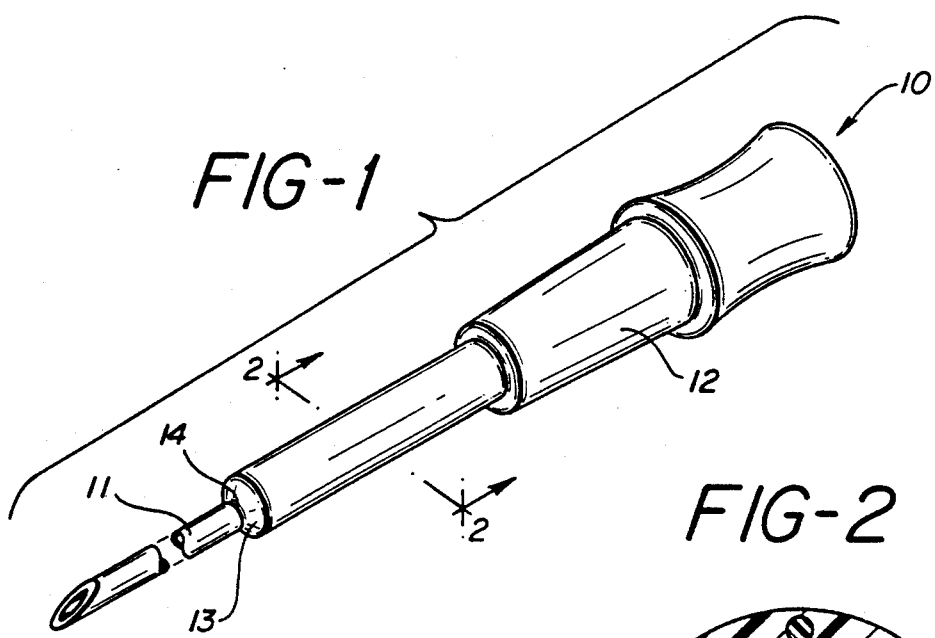
FIG-1
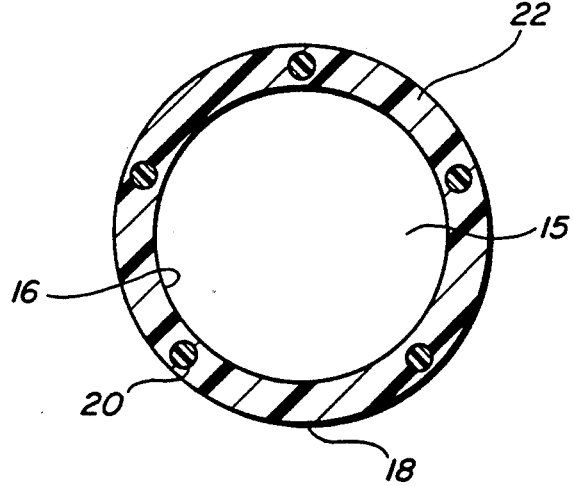
FIG-2
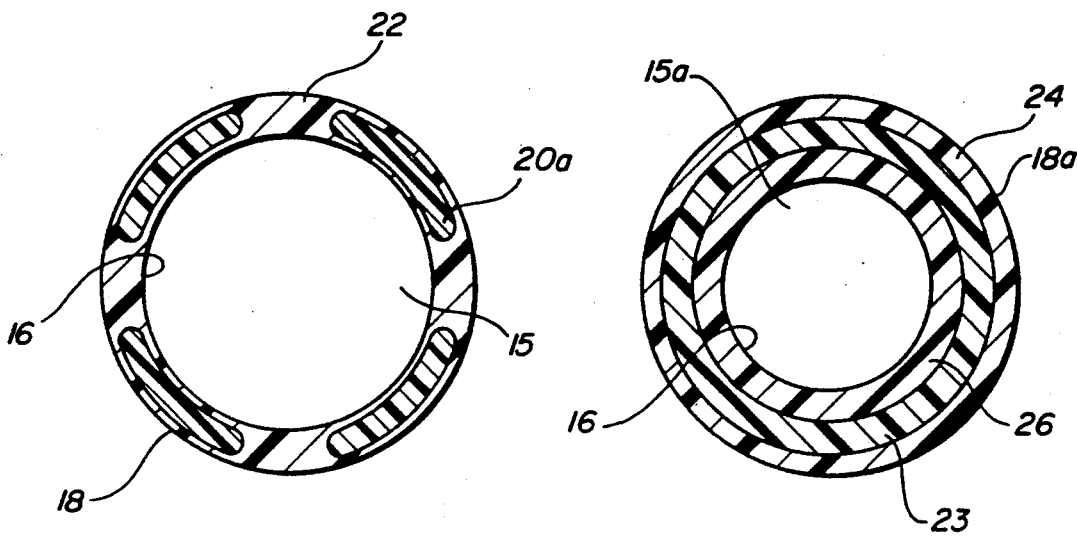
FIG-3
FIG-4

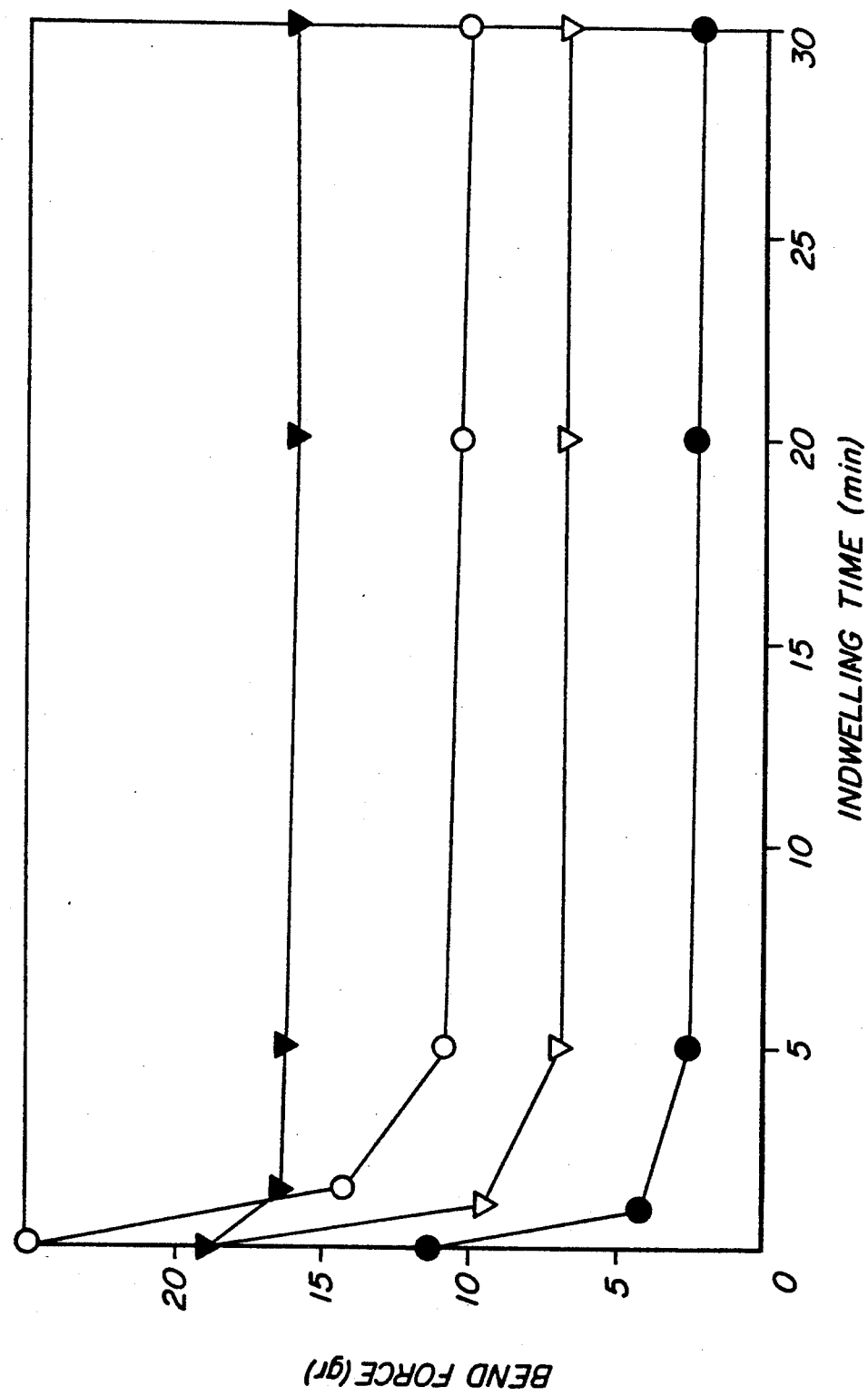

CATHETER TUBING OF CONTROLLED IN VIVO SOFTENING

This application is a continuation of application Ser. No. 07/499,145, filed Mar. 26, 1990 now abandoned.

BACKGROUND OF THE INVENTION

Field of the Invention

This invention relates to catheterization of a patient and more particularly relates to a polyurethane catheter tubing of controlled pliability when it comes into contact with a body fluid.

Background of the Invention

Catheterization procedures conventionally include puncture of a patient's skin and insertion of a catheter into a body cavity, such as the blood stream, using some type of catheter insertion device. For patient comfort, it is highly desirable that the catheter be of the smallest possible cross-sectional area during insertion. It is nevertheless evident that the catheter lumen must be large enough to achieve the required rate of administration of a medicament solution or drainage of a body fluid through the catheter.

A number of polymeric materials have been investigated for fabrication of catheter tubing. Silicone rubber has been used, but this material, which is soft and pliable, requires inclusion of various additives such as fillers and plasticizers to give sufficient tensile strength. The thick wall needed to prevent collapse due to the pliability requires a large outside diameter to achieve sufficient inside diameter for fluid flow.

Other catheters of the prior art have been made of rigid substantially inflexible polymeric materials. Exemplary of such conventional catheters are the catheters of fluorinated ethylene propylene copolymer (FEP) having stripes of FEP containing a radiopaque agent disclosed by Coneys in U.S. Pat. No. 4,657,024.

Ostoich, in U.S. Pat. No. 4,211,741, disclose a catheter having a thin layer of polyurethane laminated on either or both surfaces of a thick polyvinyl chloride layer.

Recently, hydrophilic polymers which absorb water, often termed hydrogels, have been disclosed. U.S. Pat. No. 4,668,221 to Luther discloses a catheter made of hydrophilic polymer which fits over a stylet for insertion. This catheter, on contact with blood, swells and softens so that the stylet can be removed.

U.S. Pat. No. 4,883,699 to Aniuk et al. discloses a tubing having a nonhydrophilic polyurethane component and a hydrophilic polyvinyl alcohol component. The tubing is said to absorb water and swell while retaining tensile strength.

Polyurethanes which swell and soften in contact with a body fluid have been disclosed in recent years as an attractive material for catheters. Gould et al., in U.S. Pat. No. 4,454,309, discloses hydrophilic polyurethane diacrylate compositions which swell in water and may be molded and cured to form shaped products. U.S. Pat. Nos. 4,728,322 and 4,781,703 to Walker et al. disclose catheters fabricated of a composition which includes a nonhydrophilic first component and a hydrophilic polyurethane diacrylate second component. When contacted with a liquid, the composition swells and softens due to absorption of the liquid, causing the catheter to increase in crosssectional area.

Polyurethanes as a class have several advantages as materials for catheters. In general, they have excellent blood compatibility. In addition, they absorb water, soften and thereby become more pliable. Pliability is a distinct aid in threading a catheter through a tortuous blood vessel to a desired placement.

While significant improvement in catheter performance has resulted from fabrication using polyurethane, there remains a need for a catheter having the blood compatibility, softness and pliability of polyurethane which retains sufficient mechanical strength and stiffness for ease of insertion and repositioning if desired. The present invention addresses this need.

SUMMARY OF THE INVENTION

A catheter tubing comprises a stripe or layer of a thermoplastic hydrophobic stiffening polymer encapsulated by a thermoplastic hydrophilic polyurethane base polymer. Preferred stiffening polymers are polyesters, preferably polyester-polyether block copolymers. Preferred polyurethanes are polyetherurethanes. The catheter of the invention may be fabricated by coextrusion, and may include a radiopaque agent.

The catheter of the invention retains the inherent softness and biocompatibility of polyurethane catheters, but overcomes the disadvantage of excessive pliability which may cause difficulty in repositioning conventional polyetherurethane catheters after emplacement in a blood vessel. The degree of stiffening may be controlled by the stripe or layer configuration as well as by the composition and amount of the hydrophobic stiffening polymer. Because the stiffening polymer is completely encapsulated, the blood contacts only the hemocompatible polyurethane surface. If desired, the catheter having a predetermined balance of stiffness for insertion and repositioning and pliability for threading through a blood vessel may include a radiopaque agent as a visualizing aid in emplacement and/or repositioning. The thermoplastic nature of both the stiffening and base polymers retains the economy of manufacture realized by conventional catheter design and extrusion processing.

BRIEF DESCRIPTION OF THE DRAWINGS

FIG. 1 is a perspective view of an intravenous catheter of the invention with associated catheter insertion device;

FIGS. 2, 3 and 4 are sectional views of embodiments the catheter of FIG. 1 taken along line 2—2 thereof;

FIG. 5 is a comparison of the bend force of the catheter of the invention with prior art catheters.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the invention, a polyetherurethane catheter is disclosed which provides a predetermined balance between pliability and stiffness and thus retains the advantages of polyetherurethane for overall catheter performance. The invention contemplates an intravenous catheter of any ANSI gauge size from 14

(large) to 28 (small) and a central venous (or other catheter device) of French size 4F (small) to 14F (large).

The embodiments of the catheter tubing will first be described with the aid of the figures for an intravenous catheter, with the understanding that the striped polyetherurethane tubing may equally well be used to fabricate any other type of catheter, such as a central venous, urinary or bronchial aspiration catheter. In the figures, similar elements are designated with the same reference number followed by a letter suffix.

FIGS. 1 to 3 illustrate catheter tubing 10 affixed to a conventional catheter insertion device, shown as a hollow needle 11, for penetration of a patient's skin and placement of the catheter into the patient's blood stream. Catheter insertion devices are conventional in the art and do not form a part of this invention. Tubing 10 includes a body portion 12 and a gradual taper 13 leading to its point 14 of contact with needle 11.

Tubing 10 defines a lumen 15 and has a lumen wall 16 and an outside wall 18. As seen in FIG. 2, one or more stripes 20 of a stiffening polymer are disposed longitudinally along at least a portion of the tubing length and encapsulated in a base polymer 22. While stripe 20 is illustrated in FIG. 2 as annular in shape, it may be of any other convenient shape, such as the elliptical stripes 20a shown in FIG. 3.

FIG. 4 shows an embodiment of the catheter tubing of FIG. 1 in which a layer 23 of the stiffening polymer is encapsulated by laminated layers 24 and 26 of the base polymer. Laminated layer 24 defines the outside wall 18a and laminated layer 26 defines lumen 15a and lumen wall 16a. Layers 24 and 26 may be of the same or different base polymer compositions.

The base polymer of the catheter of the invention may be any thermoplastic polymer which absorbs water for softness and flexibility and which is biocompatible and does not release any toxic products when in contact for prolonged periods with a body fluid. Suitable base polymers are also compatible for coextrusion with the stiffening polymer. While the invention contemplates use of any polymeric or copolymeric base polymer which provides these attributes, preferred base materials are hydrophilic polyurethanes.

The polyurethane base polymer may be a polyesterurethane, a silicone-urethane block copolymer or preferably a polyetherurethane and is the product from reaction of a diisocyanate, a polyglycol and a chain extender.

Suitable diisocyanates are aromatic diisocyanates such as diphenylmethane-4,4'-diisocyanate (MDI), diphenylmethane-3,3'-diisocyanate, alicyclic diisocyanates such as isophorone diisocyanate and dicyclohexylmethane-4,4'-diisocyanate, and aliphatic diisocyanates, as, for example, hexamethylene diisocyanate. The most preferred diisocyanate is MDI.

The polyglycol component may be a polyester glycol, a silicone glycol or preferably a polyether glycol or mixtures thereof. Suitable polyester glycols are, for example, polycaprolactone and polyethylene adipate. Suitable silicone glycols are, for example, polydimethylsiloxane glycols such as 4-3667 (formerly Q43667) available from Dow Corning Corp.

The preferred polyether glycol may be polytetramethyleneoxide glycol (PTMEG), alone or mixed with from 0 to 50% of polyethyleneoxide glycol (PEG) or polypropyleneoxide glycol. All percentages herein are by weight unless otherwise specified. The PEG may have a molecular weight of about 650 to 16,000, preferably about 1,000 to 4,000. The PTMEG may have a molecular weight of about 600 to 3,300 preferably about 1,000 to 2,000. Both PEG and PTMEG are readily available commercially from a variety of sources.

The chain extender may be a low molecular weight, diol (branched or unbranched) diamine or amino alcohol of up to 10 carbon atoms or mixtures thereof. Representative nonlimiting examples of chain extenders are 1,4-butanediol (BDO); ethylene glycol; diethylene glycol; triethylene glycol; 1,2-propanediol; 1,3-propanediol; 1-6-hexanediol; 1,4-bis hydroxymethyl cyclohexane, and hydroguinone dihydroxyethyl ether, 1,6-hexane diamine and ethanolamine. Preferred chain extenders are BDO and 1,6-hexanediol.

Suitable hydrophilic polyurethane base polymers have a hard segment content of about 20 to 80, preferably about 30 to 75 percent, a tensile strength of about 3,000 to 10,000 psi and a Shore hardness of at least 95 A, preferably 50 D and higher. Calculation of component ratios from a preselected hard segment and soft segment percentage to give polyurethanes within the above Shore hardness range is easily within the purview of one skilled in the art. By proper selection of hard segment and soft segment percentages and compositions, a base polymer having from about 2 to 40% water absorption for softness and flexibility, preferably about 5 to 20% may be obtained. Further, the onset of softening may be delayed by choosing a soft segment of greater hydrophobicity, or accelerated by choosing a soft segment of greater hydrophilicity.

The base polymer may be prepared by a bulk or one-shot polymerization procedure. In one suitable bulk polymerization process of the invention, conventional polymerization equipment is charged with a mixture of the polyglycol and extenders in proportions predetermined in accordance with the desired hard segment-soft segment ratio. With vigorous stirring, the diisocyanate may be added all at once. If the reaction does not start spontaneously, the mixture may be heated sufficiently to induce an exothermic reaction. The reaction mixture may be stirred vigorously until the exotherm is complete and the temperature begins to drop off, generally for about 1 to 5 minutes. The clear homogeneous melt, while still hot, may advantageously be removed from the reactor prior to curing. In an alternative procedure, the polyglycol and diisocyanate may be mixed with stirring, and, when the initial exotherm begins to subside, the extender may be added with continued stirring.

A feature of the method for preparing the base polymer of the invention is that the polymer is prepared from the components without adding a polymerization catalyst. Conventional catalysts in the art, for example, organometallic compounds such as dibutyl tin dilaurate, are leachable and may cause deleterious effects when the catheter of the invention comes into contact with a body fluid.

The stiffening polymer of the invention may be any hydrophobic polymer having a water absorption of 2% or less, a Shore hardness of 50 D and higher and compatibility for coextrusion through a die with the base polymer. As is well-known in the art, polymers are compatible for coextrusion if both can form melts for extrusion at a temperature which does not cause significant decomposition and/or melt disruption of either polymer melt when the melts pass through the die.

Suitable stiffening polymers are, for example, polyolefins, such as polyethylene, preferably high density polyethylene, and polypropylene, polyamides such as Nylon 6 and Nylon 66, polyesters such as polyethylene terephthalate and polybutylene terephthalate, high hard segment (50 to 100 weight percent) polyurethanes, polycarbonates, liquid crystalline polymers and the like. Suitable liquid crystalline polymers are for example polyphosphazines, polyxylylenes, polysulfones, polyamides, polysiloxanes and preferably polyesters. Commercially available liquid crystalline polyesters which may serve as the stiffening polymer are Vectra TM (Hoechst-Celanese, Chatham, N.J.), Xydar TM and Torlon TM (Amoco Performance Products, Ridgefield, Conn.) and LCP TM (RTP Co., Winona, Minn.).

Preferred stiffening polymers are polyetherpolyester block copolymers such as Hytrel ® (DuPont) and Riteflex ® (Hoechst Celanese) and their alloys, having a Shore D hardness of from 50 to 80. The preferred stiffening polymers are Riteflex TM 372 and Hytrel TM 7246 both having a Shore D hardness of 72.

The catheter of the invention may be fabricated from the base polymer and the stiffening polymer by any convenient coextrusion process. Suitable coextrusion apparatus may be purchased, for example, from Genca Cable Company, Clearwater, Fla., or from Wayne Machine and Die Company, Totowa, N.J., or, if desired, custom coextrusion apparatus can be designed for fabrication of any specific article of the invention.

The striped catheter of the invention may have about 1 to 12, preferably about 3 to 9, most preferably 6 stripes. If desired, one or more of the stripes may include a conventional radiopaque agent, such as bismuth trioxide or barium sulfate compounded with the stiffening polymer prior to extrusion. About 15 to 70%, preferably about 20 to 60% by weight of the radiopaque agent may be present in the stripe. Alternatively, the radiopaque agent may be melt compounded with the base polymer prior to extrusion.

In the striped catheter of the invention, the total volume percentage of the stripes may be about 10 to 80, preferably about 20 to 50 percent of the base polymer, and may conveniently be attained by choosing a coextrusion die which provides the appropriate stripe cross-section.

Likewise, the laminated catheter of the invention may contain about 10 to 90, preferably 20 to 70 volume percent of the stiffening polymer as determined by the choice of die. As described above for the striped catheter, the laminated catheter may contain a radiopaque agent in either the stiffening or base polymer.

A catheter tubing fabricated from the hydrophilic base polymer alone has stiffness for insertion and water absorption subsequent to insertion for flexibility, but may become too flexible for advancement and repositioning. It has been found that the catheter tubing of the invention provides a desirable and predetermined balance between pliability on one hand and stiffness on the other hand. This may be expressed as the bend force as determined in accordance with the procedure of Example III. Preferred catheters of the invention have a bend force of about 7–14, most preferably about 8–12 gr. FIG. 5 shows the comparative bend force of two 22 gauge commercial catheters and two 22 gauge stiffened catheters of the invention fabricated by the coextrusion process of Example II. It is seen that the bend force of the catheter of the invention falls between the two extremes.

The following examples are provided to further illustrate the invention but are not to be considered in any way as limitative.

EXAMPLE I

General Procedure for Base Polyurethane Synthesis

The calculated quantities of polyglycol and BDO required to prepare a base polyurethane having the desired hard segment content were combined in a resin bottle at 60° C., and vacuum stripped for 30 minutes at 4 mm Hg. The mixture was cooled to ambient temperature and two equivalents of MDI, based on the total hydroxyl content, was added all at once with vigorous stirring. The exotherm reached about 80° C., whereupon the mixture was poured into a Teflon-lined tray and post-cured at 110° C. for about 60 minutes.

In an alternative procedure, the polyglycol and diisocyanate may be mixed with stirring, and, when the initial exotherm begins to subside, the extender may be added with continued stirring.

EXAMPLE II

General Procedure for Preparation of Striped or Laminated Catheter by Coextrusion A base polymer melt stream from a main extruder and a stiffening polymer melt stream containing a radiopaque agent from a coextruder were maintained separately until combined as continuous stripes or layers in the forward, down stream portion of an extruder head. From the extruder head, the streams subsequently passed through and emerged from a tube die (coaxial or cross-head) as an integral tubing member.

By proper selection of extruders, coextruders and dies, the number and thickness of the stripes, layers or other configurations and thereby the volume percentages of the base polymer, stiffening polymer and the radiopaque agent was adjusted according to the requirements of the particular coextruded tubing.

EXAMPLE III

About 65% by volume of a polyetherurethane base polymer of 62% hard segment content, prepared as described in Example I, and about 35% by volume of a polyester-polyether stiffening polymer (Riteflex ® 372 and Hytrel ® 7246) containing 50% by weight of barium sulfate were coextruded to give 22 gauge 6 stripe catheters according to the procedure of Example II and the extrusion data of the Table.

TABLE

| EXTRUSION CONDITIONS | BASE POLYMER | HYTREL ® | BASE POLYMER | RITEFLEX ® |
|---|---|---|---|---|
| TIME | | | | |
| EXTRUDER | 1" | 1" | 1" | 1" |
| TEMP. °F. ZONE 1 | 380 | 349 | 381 | 320 |
| ZONE 2 | 410 | 365 | 409 | 416 |
| ZONE 3 | 425 | 376 | 425 | 430 |
| DIE 1 | 425 | 376 | 425 | 430 |
| DIE 2 | 425 | — | 425 | — |
| DIE 3 | 425 | — | 425 | — |
| MELT TEMP. °F: EXTRUDER | 427 | — | 425 | — |

TABLE-continued

| EXTRUSION CONDITIONS | BASE POLYMER | HYTREL ® | BASE POLYMER | RITEFLEX ® |
|---|---|---|---|---|
| MELT TEMP. °F: PUMP | 417 | — | 416 | — |
| BARREL PRESSURE psi | 900 | 1535 | 900 | 4000 |
| PUMP PRESSURE psi (SET POINT) | 600 | — | 600 | — |
| DIE PRESSURE psi | 1000 | — | 1000 | — |

EXAMPLE IV

Measurement of Catheter Tubing Softening

Bend force measurement was performed on two inch pieces of 22 gauge catheter tubing using the Instron Model 1122 universal testing apparatus equipped with a 200 g load cell. Compression measurements of axial force required to bend the tubing were taken after soaking the tubing in normal saline for 1, 5, 20 and 30 minutes up to 24 hours and were performed inside an environmentally controlled chamber at 37° C. and about 90-100% relative humidity. The bend force reported in grams was not correctd for tubing cross-section and reflects the stiffness/softness characteristics of actual catheterization.

Thus, the catheter of the invention combines a polyurethane surface for blood compatibility and softness for patient comfort with a balance between pliability for ease of threading through a tortuous body passage and stiffness for insertion.

What is claimed is:

1. A catheter tubing comprising a stripe of a thermoplastic hydrophobic polyester-polyether block copolymer having a Shore D hardness of about 50 to 80 encapsulated in a hydrophilic thermoplastic polyetherurethane, said polyetherurethane consisting essentially of the reaction product of 4,4'-diphenylmethane diisocyanate, polytetramethylene ether glycol and 1,4-butanediol.

* * * * *